United States Patent
Dow et al.

(10) Patent No.: US 11,648,256 B2
(45) Date of Patent: *May 16, 2023

(54) TOPICAL COMPOSITIONS AND METHODS FOR TREATING PSORIASIS

(71) Applicant: Bausch Health Ireland Limited, Dublin (IE)

(72) Inventors: Gordon J. Dow, Greenbrae, CA (US); Radhakrishnan Pillai, Santa Rosa, CA (US); Varsha D. Bhatt, San Francisco, CA (US)

(73) Assignee: Bausch Health Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/993,817

(22) Filed: Nov. 23, 2022

(65) Prior Publication Data

US 2023/0086282 A1    Mar. 23, 2023

Related U.S. Application Data

(63) Continuation of application No. 17/154,591, filed on Jan. 21, 2021, which is a continuation of application No. 16/377,540, filed on Apr. 8, 2019, now abandoned, which is a continuation of application No. 15/173,961, filed on Jun. 6, 2016, now Pat. No. 10,251,895.

(60) Provisional application No. 62/181,481, filed on Jun. 18, 2015.

(51) Int. Cl.
| | |
|---|---|
| *A61K 31/573* | (2006.01) |
| *A61K 9/00* | (2006.01) |
| *A61K 45/06* | (2006.01) |
| *A61K 9/06* | (2006.01) |
| *A61K 31/192* | (2006.01) |
| *A61K 47/26* | (2006.01) |
| *A61K 9/12* | (2006.01) |
| *A61K 47/14* | (2017.01) |
| *A61K 47/44* | (2017.01) |
| *A61K 9/107* | (2006.01) |
| *A61K 31/4436* | (2006.01) |

(52) U.S. Cl.
CPC .......... *A61K 31/573* (2013.01); *A61K 9/0014* (2013.01); *A61K 9/06* (2013.01); *A61K 9/107* (2013.01); *A61K 9/12* (2013.01); *A61K 31/192* (2013.01); *A61K 31/4436* (2013.01); *A61K 45/06* (2013.01); *A61K 47/14* (2013.01); *A61K 47/26* (2013.01); *A61K 47/44* (2013.01)

(58) Field of Classification Search
CPC .. A61K 31/56; A61K 31/566; A61K 31/4462; A61K 45/06; A61P 17/06
See application file for complete search history.

(56) References Cited

U.S. PATENT DOCUMENTS

| | | |
|---|---|---|
| 4,048,310 A | 9/1977 | Chen et al. |
| 4,083,974 A | 4/1978 | Turi |
| 4,233,295 A | 1/1980 | Hill et al. |
| 4,244,942 A | 1/1981 | Kamishita et al. |
| 4,299,828 A | 11/1981 | Wang |
| 4,370,322 A | 1/1983 | Busse et al. |
| 4,619,921 A | 10/1986 | Kalvoda et al. |
| 4,767,751 A | 8/1988 | Davis |
| 4,918,065 A | 4/1990 | Stindl et al. |
| 5,256,691 A | 10/1993 | Suzuki |
| 5,326,566 A | 7/1994 | Parab |
| 5,422,361 A | 6/1995 | Munayyer |
| 5,472,982 A | 12/1995 | Suzuki |
| 6,479,058 B1 | 11/2002 | McCadden |
| 6,517,847 B2 | 2/2003 | Dow et al. |
| 6,656,928 B1 | 12/2003 | McCadden |
| 6,730,308 B1 | 5/2004 | Sefton |
| 6,765,001 B2 | 7/2004 | Gans et al. |
| 6,974,807 B1 | 12/2005 | Sefton |
| 7,300,669 B2 | 11/2007 | Dow |
| 7,820,145 B2 | 10/2010 | Tamarkin et al. |
| 8,071,578 B2 | 12/2011 | Sefton |
| 8,808,716 B2 | 8/2014 | Loupenok |
| 8,962,028 B2 | 2/2015 | Johnson |
| 9,782,341 B2 | 10/2017 | Kulesza |
| 10,251,895 B2 * | 4/2019 | Dow ........................ A61K 9/06 |
| 10,426,787 B2 * | 10/2019 | Dow ...................... A61K 47/26 |
| 11,311,482 B2 * | 4/2022 | Angel ..................... A61P 17/00 |
| 2004/0081668 A1 | 4/2004 | Puglia |
| 2007/0196459 A1 | 8/2007 | Zhang |
| 2008/0044444 A1 | 2/2008 | Tamarkin |
| 2009/0012051 A1 | 1/2009 | Sugishita |
| 2009/0176750 A1 | 7/2009 | Gans et al. |

(Continued)

FOREIGN PATENT DOCUMENTS

| | | |
|---|---|---|
| CA | 1303991 C | 6/1992 |
| CN | 1528313 A | 9/2004 |

(Continued)

OTHER PUBLICATIONS

Afifi, T. et al., "Topical therapies for psoriasis," Canadian Family Physician, 51:519-525, 2005.

(Continued)

*Primary Examiner* — Theodore R. Howell
*Assistant Examiner* — George W Kosturko
(74) *Attorney, Agent, or Firm* — Kilpatrick Townsend & Stockton LLP

(57) ABSTRACT

Topical pharmaceutical compositions comprise a combination of a corticosteroid a retinoid; and methods for treating psoriasis with same.

30 Claims, No Drawings

(56) References Cited

U.S. PATENT DOCUMENTS

| | | |
|---|---|---|
| 2012/0129824 A1 | 5/2012 | Angel et al. |
| 2012/0328670 A1 | 12/2012 | Donello |
| 2013/0310355 A1 | 11/2013 | Kulesza |
| 2014/0349981 A1 | 11/2014 | Evers et al. |
| 2016/0367570 A1 | 12/2016 | Dow et al. |
| 2018/0177803 A1 | 6/2018 | Dow et al. |
| 2018/0360752 A1 | 12/2018 | Arturo et al. |
| 2019/0133942 A1 | 5/2019 | Arturo et al. |
| 2019/0133943 A1 | 5/2019 | Arturo et al. |
| 2019/0231797 A1 | 8/2019 | Dow et al. |
| 2021/0330681 A1 | 10/2021 | Dow et al. |

FOREIGN PATENT DOCUMENTS

| | | | | |
|---|---|---|---|---|
| CN | 1528328 | A | 9/2004 | |
| EP | 0415766 | B1 | 1/1997 | |
| EP | 2494959 | B1 | 11/2014 | |
| GB | 1563638 | | 3/1980 | |
| GB | 2050831 | | 9/1983 | |
| GB | 2122087 | | 1/1984 | |
| IN | 2461/MUM/2009 | | 3/2012 | |
| JP | S63-255227 | A | 10/1988 | |
| JP | S63-255228 | A | 10/1988 | |
| JP | H06-76328 | B2 | 9/1994 | |
| JP | 2004-359585 | A | 12/2004 | |
| NL | 7105591 | A | 10/1972 | |
| WO | 1998/36753 | A1 | 8/1998 | |
| WO | 1999/044585 | A1 | 9/1999 | |
| WO | 2000/47211 | A1 | 8/2000 | |
| WO | 2002/11683 | A1 | 2/2002 | |
| WO | 2004/058262 | A1 | 7/2004 | |
| WO | 2007/100376 | A2 | 9/2007 | |
| WO | 2008/038147 | A2 | 4/2008 | |
| WO | 2008/152444 | | 12/2008 | |
| WO | 2009/063493 | | 5/2009 | |
| WO | 2009/084020 | A2 | 7/2009 | |
| WO | 2009/158687 | A1 | 12/2009 | |
| WO | 2012/051614 | A2 | 4/2012 | |
| WO | 2012/061630 | A2 | 5/2012 | |
| WO | 2012/087443 | A1 | 6/2012 | |
| WO | WO-2012087443 | A1 * | 6/2012 | ........... A61K 31/573 |
| WO | 2015/044857 | A1 | 4/2015 | |
| WO | 2016/205001 | A1 | 12/2016 | |

OTHER PUBLICATIONS

Allergan, Inc., Label and prescribing information for Tazorac® (tazarotene) Cream, 0.05% and 0.1%, Oct. 2001, published online at <https://www.accessdata.fda.gov/drugsatfda.docs/nda/2001/21-184S001_Tazorac_prntlbl.pdf>.

Allergan, Inc., Label and prescribing information for Tazorac® (tazarotene) Cream, 0.05% and 0.1%, Dec. 2013, published online at <https://www.accessdata.fda.gov/drugsatfda_docs/label/2013/021184s007lbl.pdf>.

Allergan, Inc., Tazorac® brochure, packaging insert, revised Jul. 2017, 13 pages.

Baid, S. and L. Niemann, "Therapeutic doses of glucocorticoids: implications for oral medicine," Oral Diseases, 12:436-442, 2006.

Blum, G. and S. Yawalkar, "Multicenter, double-blind comparative observation of application of 0.02%, 0.05% CGP 14 458 ointments and dermovate ointment in the treatment of chronic psoriasis," Chinese Journal of Dermatology, 19(3):139-141, 1986 [with translation].

Bristol-Myers Squibb Company, Label and prescribing information for Ultravate® (halobetasol propionate cream) Cream, 0.05%, Apr. 2003, published online at <https://www.accessdata.fda.gov/drugsatfda_docs/label/2004/19967s010lbl.pdf>, 2 pages.

Bristol-Myers Squibb Company, Label and prescribing information for Ultravate® (halobetasol propionate ointment) Ointment, 0.05%, Apr. 2003, published online at <https://www.accessdata.fda.gov/drugsatfda_docs/label/2004/19968s007lbl.pdf>.

Budavari, S. et al. (Eds.), "4625. Halobetasol Propionate," in the Merck Index: An Encyclopedia of Chemicals, Drugs, and Biologicals, Merck & Co., Inc., 12th Ed., 1996, p. 784, 1996.

Carruthers, J. et al., "Observations on the systemic effect of topical clobetasol propionate (Dermovate)," British Medical Journal, 4:203-204, 1975.

Dermik Laboratories, Inc., Label and prescribing information for Psorcon® (diflorasone diacetate cream), 0.05%, Mar. 2002, revised Jan. 2009, published online at <https://dailymed.nlm.nih.gov/dailymed/fda/fdaDrugXsl.cfm?setid=a5fc8f9e-7813-45bc-a9d8-71d10f61d97b&type=display >.

Dhawan, S. et al., "Tazarotene cream (0.1%) in combination with betamethasone valerate foam (0.12%) for plaque-type psoriasis," J. Drugs Dermatol., 4(2):228-230, 2005.

E. Fougera & Co., Label and prescribing information for Betamethasone Dipropionate Gel, 0.05% (Augmented), Center for Drag Evaluation and Research, May 13, 2003, published online at <https://www.accessdata.fda.gov/drugsatfda_docs/anda/2003/75276_Betamethasone%20Dipropionate_Prntlbl.pdf>.

Eastman, William J. et al., "Assessing Attributes of Topical Vehicles for the Treatment of Acne, Atopic Dermatitis, and Plaque Psoriasis," Cutis, 2014, vol. 94, pp. 46-53.

Fabior® (Tazarotene) Foam 0.1% [package insert]. Research Triangle Park NC: Stiefel Laboratories, Inc.; 2012.

Fang, J. et al., "Effect of low frequency ultrasound on the in vitro percutaneous absorption of clobetasol 17-propionate," International Journal of Pharmaceutics, 191:33-42, 1999.

Feldman, S. et al., "Relative efficacy and interchangeability of various clobetasol propionate vehicles in the management of steroid-responsive dermatoses," Current Therapeutic Research, 66:154-171, 2005.

Fiume et al., Int J Toxicol. Jul.-Aug. 2012;31(4 Suppl):5S-76S.

Galderma Laboratories, L.P., Label and package insert for Clobex Lotion, 0.05% (clobetasol propionate), Jul. 24, 2003, published online at <https://www.accessdata.fda.gov/drugsatfda_docs/nda/2003/21-535_Clobex_Prntlbl.pdf>.

Gao, H. and A. Li Wan Po, "Topical formulations of fluocinolone acetonide, Are creams, gels and ointments bioequivalent and does dilution affect activity?" European Journal of Clinical Pharmacology, 46:71-75, 1994.

GlaxoWellcome Inc., Label and product information for Temovate E® (clobetasol propionate emollient cream) Emollient, 0.05%, Jul. 2000, published online at <https://www.accessdata.fda.gov/drugsatfda_docs/label/2003/020340s006lbl.pdf>.

Gollnick, H. and A. Menter, "Combination therapy with tazarotene plus a topical corticosteroid for the treatment of plaque psoriasis," British Journal of Dermatology, 140(Suppl. 54):18-23, 1999.

Guenther, Lyn C., "Optimizing Treatment with Topical Tazarotene," American Journal of Clinical Dermatology, 2003, vol. 4, No. 3, pp. 197-202.

Harding, S. et al., "Percutaneous absorption of clobetasol propionate from novel ointment and cream formulations," Clinical and Experimental Dermatology, 10:13-21, 1985.

Hecker, D. et al., "In vitro compatibility of tazarotene with other topical treatments of psoriasis," J. Am. Acad. Dermatol., 42:1008-1011, 2000.

Hu, Z. et al., "Efficacy of 0.05% CGP 14 458 ointment in the treatment of psoriasis and its effects on adrenal function," Chinese Journal of Dermatology, 21(5):291-292, 1988 [with translation].

Ismail, I. et al., "Subchronic and chronic toxicity of tazarotene gel following topical application in Hanford miniswine," International Journal of Toxicology, 16:571-584, 1997.

Kaidbey, K. et al., "A pilot study to determine the effect of tazarotene gel 0.1% on steroid-induced epidermal atrophy," International Journal of Dermatology, 40:468-471, 2001.

Kalvoda, J. et al. "Concept and development of a potent topical corticosteroid," Chimia International Journal for Chemistry, 46(7-8):338-344, 1992.

Kircik, Leon H. "Tretinoin microsphere gel pump 0.04% versus tazarotene cream 0.05% in the treatment of mild-to-moderate facial acne vulgaris," Journal of Drugs in Dermatology: JDD, Jul. 2009, vol. 8, No. 7, pp. 650-654.

(56) References Cited

OTHER PUBLICATIONS

Koo, J. et al., "Investigator-masked comparison of tazarotene gel q.d. plus mometasone furoate cream q.d. vs. mometasone furoate cream b.i.d. in the treatment of plaque psoriasis," International Journal of Dermatology, 40:210-215, 2001.
Krueger, G. et al., "The Safety and efficacy of tazarotene gel, a topical acetylenic retinoid, in the treatment of psoriasis," Arch. Dermatol., 134:57-60, 1998.
Lebwohl, M. et al., "Duration of improvement in psoriasis after treatment with tazarotene 0.1% gel plus clobetasol propionate 0.05% ointment: comparison of maintenance treatments," Int. J. Derm., 40(1):64-66, 2001.
Lebwohl, M. et al., Tazarotene 0.1% gel plus corticosteroid cream in the treatment of plaque psoriasis, J. Am. Acad. Dermatol., 39:590-6, 1998.
Lebwohl, M. et al., "Tazarotene in combination with topical corticosteroids," J. Am. Acad. Dermatol., 39:S139-43, 1998.
Lebwohl, M. et al., "Topical application of calcipotriene and corticosteroids: Combination regimens," J. Am. Acad. Dermatol., 37:S55-S58, 1997.
Leyden, James J., "Meta-Analysis of Topical Tazarotene in the Treatment of Mild to Moderate Acne," Cutis, Oct. 2004, vol. 74(suppl 4), pp. 9-15.
Loder, J. et al., "Halobetasol Propionate," in Topical Corticosteroids, S. Karger AG, Switzerland, 1992, pp. 423-434.
Lubrizol Advanced Materials, Inc., "Emulsification Properties," Pharmaceutical Bulletin 8, Oct. 29, 2008, published online at <https://www.lubrizol.com/-/media/Lubrizol/Health/Literature/Bulletin-08—Emulsification-Properties.pdf>.
Lubrizol Advanced Materials, Inc., "Introducing Pemulen® Polymeric Emulsifiers," Technical Data Sheet (TDS-114), Oct. 15, 2007, published online at <https://www.lubrizol.com/-/media/Lubrizol/Life-Sciences/Documents/TDS/TDS-114_Introducing_Pemulen_Polymeric_Emulsifiers.pdf>.
Lubrizol Advanced Materials, Inc., Product Guide and Regulatory Overview for Carbomer Homopolymer, Jun. 2011.
Medical Review, Part 2. Drug Approval Package for Tazorac (tazarotene cream). Application No. 021184. Approval Date: Sep. 29, 2000.
Medicis, Label and prescribing information for VanosTM (fluocinonide) Cream, 0.1%, Mar. 2006, published online at <https://www.accessdata.fda.gov/drugsatfda_docs/label/2006/021758s00lbl.pdf>.
Okuyama, H et al., "Influence of additives on percutaneous absorption of piroxicam from cataplasm," Drug Delivery System, 14(6):491-497, 1999 [with English translation].
O'Neil, M. et al. (Eds.), The Merck Index: An Encyclopedia of Chemicals, Drugs, and Biologicals, Merck & Co., Inc., USA, 13th ed., 1996, pp. 200-201, 413, 552, and 735.
Ostrenga, J. et al., "Vehicle design for a new topical steroid, fluocinonide," The Journal of Investigative Dermatology, 56(5):392-399, 1971.
Ozawa, Y. et al., "Influence of fatty acid-alcohol esters on percutaneous absorption of hydrocortisone butyrate propionate," Chem. Pharm. Bull., 36(6):2145-2151, 1988.
Panama Petrochemical, Safety Data Sheet for Light Liquid Paraffin, Dec. 9, 2014.
Poulin, Yves P., "Tazarotene 0.1% Gel in Combination with Mometasone Furoate Cream in Plaque Psoriasis: A Photographic Tracking Study," Cutis, Jan. 1999, vol. 63, No. 1, pp. 41-48.
Puig, L. et al., "Adherence and Patient Satisfaction With Topical Treatment in Psoriasis, and the Use, and Organoleptic Properties of Such Treatments: A Delphi Study With an Expert Panel and Members of the Psoriasis Group of the Spanish Academy of Dermatology and Venereology," Actas Dermo Sifiliograficas, 2013, vol. 104, No. 6, pp. 488-496.
Ranbaxy, Label and prescribing information for Ultravate® (halobetasol propionate) Cream, 0.05% and (halobetasol propionate) Ointment, 0.05%, Mar. 2012, published online at <https://www.accessdata.fda.gov/drugsatfda_docs/label/2012/019968s011lbl.pdf>.

Rowe, R. et al. (Eds.), Handbook of Pharmaceutical Excipients, Pharmaceutical Press and American Pharmacists Association, 6th ed., 2009, pp. 110-114, 445-449, and 675-678.
Ryatt, K. et al., "The stability and blanching efficacy of betamethasone-17-valerate in emulsifying ointment," British Journal of Dermatology 107:71-76, 1982.
Schering-Plough Pty Limited, Label and Product Information for Diprosone® OV Cream and Ointment (Betamethasone dipropionate), Aug. 26, 2008, published online at <https://www.tga.gov.au/sites/default/files/foi-065-1718-03.pdf>.
Shah, V. et al., "Bioequivalence of Topical Dermatological Products," in Topical Drug Bioavailability, Bioequivalence, and Penetration, Plenum Press, USA, 1993, pp. 393-413.
Shalita A R et al. "Tazarotene gel is safe and effective in the treatment of acne vulgaris: a multicenter, double-blind, vehicle-controlled study," Cutis, Jun. 1999, vol. 63, No. 6, pp. 349-354.
Surber, C. and A. Davis, "Bioavailability and Bioequivalence of Dermatological Formulations," in Dermatological and Transdermal Formulations, Marcel Dekker, Inc., USA, 2002, pp. 401-498.
Tanghetti, Emil et al., "Randomized Comparison of the Safety and Efficacy of Tazarotene 0.1% Cream and Adapalene 0.3% Gel in the Treatment of Patients With at Least Moderate Facial Acne Vulgaris," Journal of Drugs in Dermatology, May 2010, vol. 9, issue 5, pp. 549-558.
Taropharma, Product Monograph for Lyderm Ointment (Fluocinonide Ointment USP, 0.05%), Lyderm Gel (Fluocinonide Gel USP, 0.05%), and Lyderm Cream (Fluocinonide Cream USP, 0.05%), Sep. 2, 2003, published online at <https://pdf.hres.ca/dpd_pm/00004233.PDF>.
Thomson PDR, "Ultravate®," in Physicians' Desk Reference, Thomson PDR, USA, 58th ed., 2004, pp. 1100-1102.
U.S. National Library of Medicine (ClinicalTrials.gov), History of Changes for Study No. NCT02045277: Safety and Efficacy of IDP-118 in the Treatment of Plaque Psoriasis, Study Record Version 1, Jan. 22, 2014, published online at <https://clinicaltrials.gov/ct2/history/NCT02045277?V_1=View#StudyPageTop>.
U.S. National Library of Medicine (ClinicalTrials.gov), History of Changes for Study No. NCT02045277: Safety and Efficacy of IDP-118 in the Treatment of Plaque Psoriasis, Study Record Version 2, Feb. 19, 2014, published online at <https://clinicaltrials.gov/ct2/history/NCT02045277?V_2=View#StudyPageTop>.
U.S. National Library of Medicine (ClinicalTrials.gov), History of Changes for Study No. NCT02045277: Safety and Efficacy of IDP-118 in the Treatment of Plaque Psoriasis, Study Record Version 3, Apr. 30, 2014, published online at <https://clinicaltrials.gov/ct2/history/NCT02045277?V_3=View#StudyPageTop>.
U.S. National Library of Medicine (ClinicalTrials.gov), History of Changes for Study No. NCT02045277: Safety and Efficacy of IDP-118 in the Treatment of Plaque Psoriasis, Study Record Version 4, Dec. 8, 2014, published online at <https://clinicaltrials.gov/ct2/history/NCT02045277?V_4=View#StudyPageTop>.
U.S. National Library of Medicine (ClinicalTrials.gov), History of Changes for Study No. NCT02045277: Safety and Efficacy of IDP-118 in the Treatment of Plaque Psoriasis, Study Record Version 5, Aug. 15, 2016, published online at <https://clinicaltrials.gov/ct2/history/NCT02045277?V_5=View#StudyPageTop>.
U.S. National Library of Medicine (ClinicalTrials.gov), History of Changes for Study No. NCT02045277: Safety and Efficacy of IDP-118 in the Treatment of Plaque Psoriasis, Comparison of Study Record Version 4, Dec. 8, 2014, and Version 5, Aug. 15, 2016, published online at <https://clinicaltrials.gov/ct2/history/NCT02045277?A=4&B=5&C=Side-by-Side#StudyPageTop>.
U.S. National Library of Medicine (ClinicalTrials.gov), History of Changes for Study No. NCT02045277: Safety and Efficacy of IDP-118 in the Treatment of Plaque Psoriasis, Study Record Version 6, Dec. 13, 2017, published online at <https://clinicaltrials.gov/ct2/history/NCT02045277?V_6=View#StudyPageTop>.
U.S. National Library of Medicine (ClinicalTrials.gov), History of Changes for Study No. NCT02045277: Safety and Efficacy of IDP-118 in the Treatment of Plaque Psoriasis, Study Record Version 7, Aug. 8, 2020, published online at <https://clinicaltrials.gov/ct2/history/NCT02045277?V_7=View#StudyPageTop>.

(56) References Cited

OTHER PUBLICATIONS

U.S. National Library of Medicine (ClinicalTrials.gov), History of Changes for Study No. NCT01670513: A Phase 2 Dosing Ranging, Evaluator-Blinded Study to Evaluate the Safety of Topical IDP-118, Study Record Version 1, Aug. 20, 2012, published online at <https://clinicaltrials.gov/ct2/history/NCT01670513?V_1=View#StudyPageTop>.

U.S. National Library of Medicine (ClinicalTrials.gov), History of Changes for Study No. NCT01670513: A Phase 2 Dosing Ranging, Evaluator-Blinded Study to Evaluate the Safety of Topical IDP-118, Study Record Version 2, Apr. 23, 2013, published online at <https://clinicaltrials.gov/ct2/history/NCT01670513?V_2=View#StudyPageTop>.

U.S. National Library of Medicine (ClinicalTrials.gov), Study Record Detail: Tabular View, Study No. NCT02045277: Safety and Efficacy of IDP-118 in the Treatment of Plaque Psoriasis, Aug. 20, 2020, published online at <https://clinicaltrials.gov/ct2/show/record/NCT02045277?term=NCT02045277&draw=2&rank=1>.

U.S. National Library of Medicine (ClinicalTrials.gov), Study Record Detail: Study Results, Study No. NCT02045277: Safety and Efficacy of IDP-118 in the Treatment of Plaque Psoriasis, Aug. 20, 2020, published online at <https://clinicaltrials.gov/ct2/show/results/NCT02045277?term=NCT02045277&draw=2&rank=1>.

U.S. National Library of Medicine (ClinicalTrials.gov), Study Record Detail: Study Details, Study No. NCT01670513: A Phase 2 Dosing Ranging, Evaluator-Blinded Study to Evaluate the Safety of Topical IDP-118, Apr. 25, 2013, published online at <https://clinicaltrials.gov/ct2/show/study/NCT01670513>.

U.S. National Library of Medicine (ClinicalTrials.gov), Study Record Detail: No Results Posted, Study No. NCT01670513: A Phase 2 Dosing Ranging, Evaluator-Blinded Study to Evaluate the Safety of Topical IDP-118, Apr. 25, 2013, published online at <https://clinicaltrials.gov/ct2/show/results/NCT01670513>.

U.S. National Library of Medicine (ClinicalTrials.gov), Study Record Detail: Tabular View, Study No. NCT01670513: A Phase 2 Dosing Ranging, Evaluator-Blinded Study to Evaluate the Safety of Topical IDP-118, Apr. 25, 2013, published online at <https://clinicaltrials.gov/ct2/show/record/NCT01670513>.

Weinberg, J. (ed.), Treatment of Psoriasis, Birkhäuser Verlag AG, Switzerland, 2008, pp. 1-70.

Westwood-Squibb Pharmaceuticals Inc., Patient information leaflet for Ultravate® (halobetasol propionate cream) Cream, 0.05%, 1995, published online at <https://www.accessdata.fda.gov/drugsatfda_docs/label/2003/019967s004lbl.pdf>.

Zografi, G. et al., "Interfacial Phenomena," in Remington's Pharmaceutical Sciences, Mack Publishing Co., USA, 18th ed., 1990, pp. 257-309.

U.S. District Court, District of New Jersey, Opinion, *Bausch Health Ireland Limited* v. *Padagis Israel Pharmaceuticals Ltd*, Case 2:20-cv-05426-SRC-CLW Document 246 Filed Dec. 1, 2022, 77 pages.

* cited by examiner

TOPICAL COMPOSITIONS AND METHODS FOR TREATING PSORIASIS

RELATED APPLICATIONS

This application is a continuation of U.S. patent application Ser. No. 17/154,591, filed Jan. 21, 2021, which is a continuation of U.S. patent application Ser. No. 16/377,540, filed Apr. 8, 2019, which is a continuation of U.S. patent application Ser. No. 15/173,961, which issued as U.S. Pat. No. 10,251,895 on Apr. 9, 2019, and which claims the benefit of U.S. Provisional Patent Application No. 62/181,481, filed on Jun. 18, 2015, the disclosures of which are incorporated herein by reference in their entirety for all purposes.

BACKGROUND OF THE INVENTION

The present invention relates to topical compositions and methods for treating psoriasis. In particular, this invention relates to topical pharmaceutical compositions comprising a combination of active ingredients, and methods using the same, for treating psoriasis. More particularly, this invention relates to topical pharmaceutical compositions comprising a combination of a corticosteroid and a retinoid, and methods using the same, for treating psoriasis.

Psoriasis is a chronic skin disease affecting approximately about 2-4 percent of the population worldwide. Over seven million people in the United States are affected. While the pathogenesis of psoriasis has not yet been fully elucidated, significant evidence indicates that epidermal changes occur as a secondary response to cellular immune infiltrates in the skin. Psoriasis is characterized by discrete areas of skin inflammation with redness, thickening, intense scaling, and in some cases, itching. The disease has significant impact on the quality of life of affected individuals, both physically and psychologically. Today there is no cure for psoriasis, and treatment is directed at reducing the severity and extent of the psoriatic plaques and the related symptoms. The primary measurement of treatment success used by the U.S. Food and Drug Administration in evaluating products for the treatment of psoriasis is significant overall improvement in psoriasis severity based on Investigators Global Assessment.

Systemic therapy such as methotrexate, or biologics such as etanercept, adalimumab, infliximab, etc. are the preferred treatment when the skin involvement is extensive; e.g., ten percent of the body surface area or more. A large number of those suffering from psoriasis have less extensive disease, and topical medications are considered a safer and more prudent alternative in most of these cases. Among the topical therapies are anti-inflammatory corticosteroids; particularly, the super potent ones such as halobetasol propionate, vitamin D derivatives, such as calcipotriene, a retinoid known as tazarotene, and coal tar. Each of the topical therapies has some degree of effectiveness, but each has limitations in the degree of improvement of the psoriatic plaques that can be achieved or the occurrence of adverse effects.

Halobetasol propionate (a topical corticosteroid) is commercially available and has been used to treat psoriasis for about 20 years or more at strength of 0.05% in a variety of dosage forms such as creams and ointments. Halobetasol is quite effective in improving the signs and symptoms of psoriasis; however both local and systemic adverse effects limit its chronic use. Treatment duration is limited to 2 weeks by FDA, and signs and symptoms of psoriasis often rebound (worsen) following the end of treatment.

For many years tazarotene (a retinoid) has been commercially available and has been used to treat psoriasis topically as creams and gels of 0.05% and 0.1%. Tazarotene generally shows moderate effectiveness in psoriasis; however its use in psoriasis is severely limited by local skin irritation. Dermatologists treated psoriasis and achieved good clinical results using sequential therapy with a corticosteroid in the morning and tazarotene applied in the evening.

The need still exists for more effective and safer topical medicaments with reduced adverse effects for the management of psoriasis.

SUMMARY OF THE INVENTION

In general, the present invention provides topical compositions and methods for treating psoriasis.

In one aspect, the present invention provides topical pharmaceutical compositions comprising a combination of active ingredients selected from the group consisting of dermatological immune response-modulating agents and anti-proliferative agents, and methods using the same, for treating psoriasis.

In another aspect, the present invention provides topical pharmaceutical compositions comprising a combination of: (a) a corticosteroid or a pharmaceutically acceptable salt or ester thereof; and (b) a retinoid or a pharmaceutically acceptable salt or ester thereof, and methods using the same, for treating psoriasis. In one embodiment, such psoriasis is plaque psoriasis.

In still another aspect, the present invention relates to topical pharmaceutical compositions comprising a combination of: (a) halobetasol or a pharmaceutically acceptable salt or ester thereof; and (b) tazarotene or a pharmaceutically acceptable tazarotenic acid salt, and methods using the same, for treating psoriasis. In one embodiment, such psoriasis is plaque psoriasis.

In yet another aspect, the present invention provides topical pharmaceutical compositions comprising a combination of: (a) halobetasol or a pharmaceutically acceptable salt or ester thereof; and (b) a tazarotene or a pharmaceutically acceptable tazarotenic acid salt or a pharmaceutically acceptable non-ethyl ester of tazarotenic acid, and methods using the same, for treating psoriasis; wherein each of: (a) halobetasol or a pharmaceutically acceptable salt or ester thereof; and (b) tazarotene or a pharmaceutically acceptable tazarotenic acid salt or a pharmaceutically acceptable non-ethyl ester of tazarotenic add is present in the composition at a positive concentration of less than 0.09% based on the weight of the composition. A non-ethyl ester of tazarotenic acid is an ester of tazarotenic acid that is not the ethyl ester. For example, a non-ethyl ester can be methyl, propyl, isopropyl, butyl, isobutyl, pentyl, isopentyl, aryl, phenyl, or naphthyl ester. In one embodiment, the concentration of halobetasol or a pharmaceutically acceptable salt is in the range from about 0.001 to about 0.049 weight percent ("wt %"); and the concentration of tazarotene or a pharmaceutically acceptable tazarotenic acid salt is in the range from about 0.001 to about 0.049 wt %.

Other features and advantages of the present invention will become apparent from the accompanying drawings and the following detailed description and claims.

DETAILED DESCRIPTION OF THE INVENTION

In general, the present invention provides topical compositions and methods for treating psoriasis.

Throughout this disclosure, unless otherwise indicated, the concentration of an ingredient of the composition is in percent by weight of the total composition.

In one aspect, the present invention provides topical pharmaceutical compositions comprising a combination of active ingredients selected from the group consisting of dermatological immune response-modulating agents and anti-proliferative agents, and methods using the same, for treating psoriasis.

In another aspect, a topical pharmaceutical composition of the present invention is used to treat or ameliorate psoriasis in patients suffering from moderate to severe plaque psoriasis.

In yet another aspect, a topical pharmaceutical composition of the present invention is used to treat or ameliorate psoriasis in patients with psoriasis covering up to about 12 percent of the body surface area.

The inventors have unexpectedly discovered that a topical dermatological composition comprising two different active ingredients selected from the group consisting of dermatological immune response-modulating agents and anti-proliferative agents is synergistically more efficacious than the combined efficacies of compositions, each comprising only one of the active ingredients in the treatment of psoriasis. In one aspect, one active ingredient is a corticosteroid, and the other active ingredient is a retinoid. Corticosteroids are also known alternatively as steroids, corticoids or glucocorticosteroids.

In particular, the inventors surprisingly discovered that a composition comprising halobetasol (a corticosteroid) and tazarotene (a retinoid) is synergistically more efficacious than the combined efficacies (i.e., the sum of the efficacies) of compositions, each comprising only one of these active ingredients.

In another aspect, the present invention provides topical pharmaceutical compositions comprising a combination of: (a) a corticosteroid or a pharmaceutically acceptable salt or ester thereof; and (b) a retinoid or a pharmaceutically acceptable salt or ester thereof, and methods using the same, for treating psoriasis.

In one aspect, a corticosteroid included in a composition of the present invention is selected from the corticosteroids of class 1. The classification of corticosteroids and examples thereof are disclosed in Table 1.

TABLE 1

| Class 1 - Superpotent Topical Corticosteroids |
| --- |
| Clobetasol propionate |
| Betamethasone dipropionate |
| Halobetasol propionate |
| Fluocinonide |
| Diflorasone diacetate |

Clobetasol propionate and halobetasol propionate have been used for treating steroid responsive dermatoses, including psoriasis, always at a concentration of 0.05%, in various dosage forms including ointments, creams, solutions, sprays, and gels.

Betamethasone dipropionate has been used for treating steroid responsive dermatoses, including psoriasis, always at a concentration of 0.064% equivalent to 0.05% betamethasone, in several dosage forms including ointments, creams, gels and lotions.

Fluocinonide has been used for treating steroid responsive dermatoses, including psoriasis, at various concentrations ranging from 0.001% to 0.1%, in various dosage forms including ointments, creams, gels and solutions. Only the 0.1% formulations have been classified as superpotent.

Diflorasone diacetate has been used for treating steroid responsive dermatoses, including psoriasis, at various concentration of 0.05%, as an ointment and as a cream. Only ointment formulation has been classified as superpotent.

HPA axis suppression from long term use topical preparations containing clobetasol propionate and halobetasol propionate and other super potent corticosteroids has limited the duration of therapy allowed by FDA. The duration on therapy allowed in the labeling for super potent topical corticosteroids is normally limited to two weeks.

In one aspect, the corticosteroid is present at a concentration below that which is presently utilized in topical formulations. The formulation contains the corticosteroid at a positive concentration less than 0.05% w/w.

In certain embodiments of the present invention, a corticosteroid or a pharmaceutically acceptable salt or ester thereof is present in the composition at a positive concentration of less than 0.05% based on the weight of the composition. Alternatively, the corticosteroid is present in the composition at a concentration in the range from about 0.001 to about 0.049 wt %, or from about 0.005 to about 0.04 wt %, or from about 0.005 to about 0.035 wt %, or from about 0.005 to about 0.03 wt %, or from about 0.005 to about 0.025 wt %, or from about 0.005 to about 0.015 wt %, or from about 0.005 to about 0.01 wt %.

In still another aspect, a retinoid included in a composition of the present invention is selected from the group consisting of tazarotene, bexarotene, and adapalene. These retinoids are commonly known as third-generation retinoids.

In yet another aspect, a retinoid belonging to the group known as second-generation retinoids (such as etretinate and acitretin) may be used in a composition of the present invention for patients who suffer from the psoriatic condition.

In one aspect, the retinoid is present at a concentration below that which is presently utilized in topical formulations. For example, tazarotene or tazarotenic acid salt is included in a composition of the present invention at a positive concentration less than 0.05 wt %.

In certain embodiments of the present invention, a retinoid or a pharmaceutically acceptable salt or ester thereof is present in the composition at a positive concentration of less than 0.09% based on the weight of the composition. For example, the retinoid is present in the composition at a concentration in the range from about 0.001 to about 0.09 wt %, or from about 0.001 to about 0.08 wt %, or from about 0.001 to about 0.07 wt %, or from about 0.001 to about 0.06 wt %, or from about 0.01 to about 0.09 wt %, or from about 0.01 to about 0.08 wt %, or from about 0.01 to about 0.07 wt %, or from about 0.01 to about 0.06 wt %, or from about 0.001 to about 0.049 wt %, or from about 0.005 to about 0.045 wt %, or from about 0.005 to about 0.04 wt %, or from about 0.005 to about 0.03 wt %, or from about 0.005 to about 0.02 wt %, or from about 0.005 to about 0.01 wt %, or from about 0.01 to about 0.049 wt %, or from about 0.01 to about 0.045 wt %, or from about 0.02 to about 0.045 wt %, or from about 0.03 to about 0.045 wt %.

In another aspect, the pharmaceutical composition comprises a combination of: (a) halobetasol or a pharmaceutically acceptable salt or ester thereof; and (b) a tazarotene or a pharmaceutically acceptable tazarotenic acid salt or a pharmaceutically acceptable non-ethyl ester of tazarotenic acid, for treating psoriasis; wherein (a) halobetasol or a pharmaceutically acceptable salt or ester thereof is present in the composition at a concentration in the range from about 0.005 to about 0.035 wt %, or from about 0.005 to about 0.025 wt %, or from about 0.01 to about 0.025 wt %; and (b) tazarotene or a pharmaceutically acceptable tazarotenic acid salt or a pharmaceutically acceptable non-ethyl ester of tazarotenic acid is present in the composition at a concentration in the range from about 0.001 to about 0.049 wt %, or from about 0.01 to about 0.049 wt %, or from about 0.01 to about 0.045 wt %, or from about 0.02 to about 0.04 wt %, or from about 0.02 to about 0.045 wt %, or from about 0.03 to about 0.045 wt %.

In still another aspect, the pharmaceutical composition comprises a combination of: (a) halobetasol or a pharmaceutically acceptable salt or ester thereof at a concentration of 0.01 wt %; and (b) tazarotene at a concentration of 0.045 wt %, or a pharmaceutically acceptable tazarotenic acid salt at a concentration that provides 0.045 wt % as tazarotene, for treating psoriasis.

In still another aspect, the pharmaceutical composition comprises a combination of: (a) halobetasol or a pharmaceutically acceptable salt or ester thereof at a concentration of 0.01 wt %; and (b) tazarotene at a concentration of 0.045 wt %, or a pharmaceutically acceptable ester, other than ethyl ester, of tazarotenic acid at a concentration that provides 0.045 wt % as tazarotene, for treating psoriasis. Non-limiting examples of non-ethyl esters of tazarotenic acid are disclosed herein above.

In yet another aspect, the pharmaceutical composition comprises a combination of: (a) halobetasol propionate at a concentration of 0.01 wt %; and (b) tazarotene at a concentration of 0.045 wt %, for treating psoriasis.

In one aspect, a topical pharmaceutical composition of the present invention is in the dosage form of gel, emulsion (including lotion, cream, and milk), shampoo, foam, suspension, liquid, spray, paste or ointment. In certain preferred embodiments, a topical pharmaceutical composition of the present invention is an oil-in-water emulsion, in which an internal oil phase is dispersed in a continuous aqueous phase. Alternatively, water-in-oil-in-water, water-in-oil and oil-in-water-in-oil emulsions are also contemplated. The emulsion may be a macroemulsion, a microemulsion, or a nanoemulsion. Also contemplated are other formulations in which an oil phase and a water phase coexist within the formulation, such as a multivesicular emulsion, which is not a true emulsion, disclosed in Espinoza, U.S. Pat. No. 6,709,663. Also contemplated is a liposomal dispersion in a gel, cream or other dosage form. Also contemplated are other formulations in which non-polar and polar liquid ingredients, with or without semipolar ingredients, coexist with the formulation.

In addition to the active ingredients as disclosed above, a composition of the present invention comprises one or more dermatologically acceptable excipients, such as liquid oils, waxes viscosity-modifying agents, thickening agents, gelling agents, alcohols, surfactants, chelating agents, buffers, preservatives, humectants, emollients, stabilizers, diluents, dispersing agents, emulsifiers, wetting agents, stabilizers, pH adjusters, solvents or cosolvents.

The formulation of the invention may desirably contain a thickening agent to provide viscosity so that the formulation may be provided in the form of a lotion, gel, cream, or ointment. Preferably, but not necessarily, the thickening agent is miscible or soluble in an aqueous fluid. Non-limiting examples of suitable thickening agents include acacia, alginic acid and its salts, hyaluronic acid and its salts, carbomers (also known as carboxy vinyl polymers, which are cross-linked polyacrylic acid), carboxymethylcellulose, ethylcellulose, gelatin, hydroxyethyl cellulose, hydroxypropyl cellulose, hydroxypropylmethyl cellulose, methylcellulose, poloxamers, polyvinylpyrrolidone, polyvinyl alcohol, tragacanth, xanthan gum, magnesium aluminum silicate, and bentonite. The thickening agent may also reside in the oil or lipophilic portion of the formulation. Examples of suitable lipophilic thickening agents include cetyl alcohol, stearyl alcohol, glyceryl stearate, white beeswax, microcrystalline wax, hydrogenated polyisobutane polymers, and emulsifying wax.

A suitable group of thickening agents is carbomers, such as Carbopol® and polycarbophil (The Lubrizol Corporation, Wickliffe, Ohio). Carbopol® homopolymers are polymers of acrylic acid crosslinked with allyl sucrose or allylpentaerythritol. Carbopol® copolymers are polymers of acrylic acid and $C_{10}$-$C_{30}$ alkyl acrylate crosslinked with allylpentaerythritol. Carbopol® interpolymers are carbomer homopolymers or copolymers that contain a block copolymer of polyethylene glycol and a long chain alkyl acid ester. Noveon® polycarbophil is a polymer of acrylic acid crosslinked with divinyl glycol.

A surfactant or emulsifier is included, if desired or required. Pharmaceutically acceptable anionic, cationic, or non-ionic surfactants may be included in a composition of the present invention. Non-ionic surfactants are preferred. Non-limiting examples of non-ionic surfactants are Octoxynol (also known as Macrogol tetramethylbutylphenyl ether, octylphenoxy polyethoxyethanol, or polyoxyethylene octylphenyl ether), such as Octoxynol 1, 3, 5, 8, 9, 10, 12, 13, 16, 30, 40, 70 (wherein the number indicates the number of repeating oxyethylene units), or other Octoxynols that comprise different numbers of repeating units of oxyethylene in the side chain, sorbitan esters (such as sorbitan monooleate and sorbitan monostearate, commonly known by their trade names Span 80 and Span 60), polysorbates (such as polysorbate 80 (polyoxyethylene sorbitan monooleate), polysorbate 60 (polyoxyethylene sorbitan monostearate), polysorbate 20 (polyoxyethylene sorbitan monolaurate), commonly known by their trade names of Tween® 80, Tween® 60, Tween® 20), poloxamers (synthetic block polymers of ethylene oxide and propylene oxide, such as those commonly known by their trade names of Pluronic®; e.g., Pluronic® F127 or Pluronic® F108), or poloxamines (synthetic block polymers of ethylene oxide and propylene oxide attached to ethylene diamine, such as those commonly known by their trade names of Tetronic®; e.g., Tetronic® 1508 or Tetronic® 908, etc.), other nonionic surfactants such as Brij® (polyoxyethylene alkyl ether having a formula of $CH_3-(CH_2)_{10-16}-(O-C_2H_4)_{1-25}-OH$), Myrj® (stearic acid esterified with polyoxyethylene having 40-100 repeating oxyethylene units), and long chain fatty alcohols (e.g., oleyl alcohol, stearyl alcohol, myristyl alcohol, docosahexaenoyl alcohol, etc.) with carbon chains having about 12 or more carbon atoms (e.g., such as from about 12 to about 24 carbon atoms).

In addition, polymeric emulsifiers such as those known under the trade name Pemulen™ (The Lubrizol Corporation, Wickliffe, Ohio) may be used. These are polymers of acrylic acid, modified by long chain ($C_{10}$-$C_{30}$) alkyl acrylates, and crosslinked with allylpentaerythritol.

An anionic emulsifier may be used, such as sodium or potassium oleate, triethanolamine stearate, sodium lauryl sulfate, sodium dioctyl sulfosuccinate, and sodium docusate. Less preferred are cationic emulsifiers such as quaternary ammonium salts. Still other emulsifiers include glyceryl monostearate, polyoxyethylene monooleate, polyoxyethylene monostearate, polyoxyethylene monolaurate, potassium oleate, sodium lauryl sulfate, sodium oleate, sorbitan monolaurate, sorbitan monopalmitate, sorbitan monostearate, sorbitan tristearate, sorbitan monooleate, sorbitan trioleate, triethanolamine oleate, polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, and polyoxyethylene sorbitan trioleate.

The formulation desirably contains a dermatologically acceptable humectant such as glycerin, sorbitol, hexylene glycol, propylene glycol, or urea. In addition, the formulation may contain an emollient such as petrolatum, lanolin, mineral oil, light mineral oil, stearic acid, cyclomethicone, or dimethicone. Chelating agents such as EDTA and its salts may be included in a formulation of the present invention.

The liquid oil component of the composition includes one or more materials that are practically insoluble or insoluble in water and which are liquid at room temperature. For example, in one embodiment, the liquid oil component of the composition includes one or more materials that are practically insoluble or insoluble in water and which are liquid at room temperature of 22° C. The liquid oil component may be selected from one or more ingredients from the group consisting of dicarboxylic acid esters ("DCAE"), monocarboxylic acid esters ("MCAE"), fish-liver oil, long-chain triglycerides (wherein each side chain has 14-18 carbons, such as peanut oil, sesame oil, coconut oil, sunflower oil, corn oil, olive oil, cotton seed oil, or derivatives thereof), propylene glycol diesters, medium-chain triglycerides (such as those wherein each side chains has 8-10 carbons; e.g., capric/caprylic acid triglycerides), hydrocarbons like mineral oil, light mineral oil, squalene, and squalane, fatty alcohols (such as octyldodecanol and isostearyl alcohol), and fatty acids (such as isostearic acid and oleic acid).

In some embodiments, the liquid oil component comprises a dicarboxylic acid ester and light mineral oil. In some other embodiments, the liquid oil component comprises one or more long-chain triglycerides.

The formulation may include other lipophilic liquids in an amount that is sufficient to be miscible with the dicarboxylic acid ester and/or monocarboxylic acid ester. The lipophilic liquid may be an emollient such as lanolin oil, mineral oil, light mineral oil, isostearic acid, squalene, octyldodecanol, fractionated coconut oil, cyclomethicone, or dimethicone.

In addition to the liquid oil component, the formulation may contain water insoluble or practically insoluble ingredients that are not liquid at room temperature, but are soluble in the liquid oil component.

A DCAE that is suitable for the present invention has the formula $R_1OOC\text{—}(CH_2)_n\text{—}COOR_2$, wherein $R_1$ and $R_2$ are alkyl groups containing between 1 and 4 carbons or aryl groups and may be the same or may be different and wherein $(CH_2)_n$ is a straight or branched chain and n is between 1 and 12. Examples of DCAEs containing one or more aryl groups are dibenzyl esters of dicarboxylic acids. A preferred dicarboxylic acid ester is diethyl sebacate, which has the formula $CH_3CH_2OOC\text{—}(CH_2)_8\text{—}COOCH_2CH_3$. Examples of other suitable dicarboxylic acid esters (where $R_1$ and $R_2$ are the same) are dimethyl, diethyl, dipropyl, diisopropyl, dibutyl and diisobutyl esters such as oxalate, malate, succinate, glutarate, adipate, pimelate, suberate, and azalate. Examples of suitable dicarboxylic acid esters (where $R_1$ is different from $R_2$) are methyl ethyl, methyl propyl, methyl butyl, methyl isopropyl, ethyl propyl, ethyl butyl, ethyl isopropyl, and propyl butyl esters such as oxalate, malate, succinate, glutarate, adipate, pimelate, suberate, azalate, and sebacate.

Alternatively, or in combination with the DCAE, the formulation may contain a MCAE. The MCAE that is suitable for the present invention has the formula $CH_3\text{—}(CH_2)_n\text{—}COOR_1$, wherein $R_1$ is an alkyl group containing between 1 and 4 carbons or an aryl group, and wherein $(CH_2)_n$ is straight or branched chain and n is between 1 and 12. Examples of such monocarboxylic acid esters include methyl, ethyl, propyl, isopropyl, butyl, or an aryl such as benzyl formate, acetate, propionate, butyrate, valerate, laurate, myristate, palmitate, and stearate. Examples of preferred monocarboxylic acid esters are isopropyl palmitate and isopropyl myristate.

The liquid oil phase may beneficially be used to dissolve one or more of the active ingredients within the emulsion or other type of formulation of the present invention. In one embodiment the corticosteroid and the retinoid are both dissolved in the liquid oil phase within the formulation at room temperature. In another embodiment the corticosteroid is dissolved in the liquid oil phase and the retinoid is suspended within the formulation at room temperature. In yet another embodiment the retinoid is dissolved in the liquid oil phase and the corticosteroid is suspended within the formulation at room temperature. In the case wherein the retinoid or the corticosteroid is suspended in the formulation, it is preferred that the suspended active ingredient be micronized, namely that the mean particle size is preferably about 25 microns in diameter or less.

In one aspect, a composition of the present invention comprises the ingredients at the concentrations shown in Table 2.

TABLE 2

Compositions of the Present Invention for Treating Psoriasis

| Ingredient | Concentration (wt %) | | |
| --- | --- | --- | --- |
| | Range 1 | Range 2 | Range 3 |
| Class-1 Corticosteroid | 0.001-0.049 | 0.005-0.035 | 0.01-0.025 |
| Tazarotene or Tazarotenic Acid Compound | 0.01-0.049 | 0.02-0.045 | 0.03-0.045 |
| Emollient, Solvent, and/or Thickener | 0.5-40 | 1-25 | 2-20 |
| Emulsifier | 0.25-10 | 0.5-7 | 1-5 |
| Humectant | 0-15 | 2-12 | 10 |
| Polymeric Thickener | 0.05-2 | 0.1-1.5 | 0.3-1 |
| Pharmaceutical Aids | q.s. | q.s. | q.s. |
| Purified water | q.s. to 100 | q.s. to 100 | q.s. to 100 |

Non-limiting examples of compositions of the present invention are shown in Table 3.

TABLE 3

Some Emulsion Compositions of the Present Invention for Treating Psoriasis

| Ingredient | Function | Concentration (wt %) | | | |
|---|---|---|---|---|---|
| | | Range 1 | Range 2 | Range 3 | Preferred embodiment |
| Halobetasol propionate | Class 1 Corticosteroid | 0.001-0.04 | 0.005-0.03 | 0.005-0.02 | 0.01 |
| Tazarotene | Retinoid | 0.02-0.049 | 0.03-0.049 | 0.04-0.049 | 0.045 |
| Diethyl sebacate | Liquid Oil & Solvent | 1-5 | 2-4 | 2.5-3.5 | 2.97 |
| Light mineral oil | Liquid Oil & Co-Solvent | 5-15 | 5-10 | 7.5-8.5 | 8.03 |
| Sorbitan monooleate | Surfactant/ Emulsifying Agent | 0.01-1 | 0.02-0.5 | 0.05-0.2 | 0.1 |
| Sorbitol solution, 70% | Humectant | 5-15 | 7-12 | 10-11 | 10.7 |
| Methyl paraben | Antimicrobial Preservative[1] | 0.05-0.3 | 0.1-0.3 | 0.1-0.2 | 0.17 |
| Propyl paraben | Antimicrobial Preservative[1] | 0.01-0.1 | 0.01-0.05 | 0.02-0.04 | 0.03 |
| Edetate disodium dihydrate | Chelating Agent[1] | 0.02-0.1 | 0.02-0.7 | 0.03-0.06 | 0.05 |
| Carbomer copolymer type B (e.g., Pemulen ™ TR-1) | Emulsifying Agent | 0.1-1 | 0.2-0.7 | 0.3-0.5 | 0.4 |
| Carbomer homopolymer type A (e.g., Carbomer 981) | Thickener | 0.2-1.5 | 0.3-1 | 0.5-0.7 | 0.6 |
| Sodium hydroxide, 10% Solution | pH-adjusting Agent[1] | q.s. to pH of 5.5 ± 0.5 | q.s. to pH of 5.5 ± 0.5 | q.s. to pH of 5.5 ± 0.5 | q.s. to pH of 5.5 ± 0.5 |
| Purified water | Carrier | q.s. to 100 | q.s. to 100 | q.s. to 100 | q.s. to 100 |

Note:
[1]These ingredients are broadly classified as Pharmaceutical Aids.

A lotion having a composition as shown in the last column of Table 2 was prepared as follows.

A separate aqueous phase was made. In a manufacturing vessel equipped with a mixing implement (such as a propeller) and temperature control, purified water and disodium edetate dihydrate were combined and the mixture was agitated until a clear solution is achieved. Sorbitol, methylparaben, and propylparaben were then added to the mixture. The mixture was continuously mixed and was heated to approximately 75° C. The mixture was agitated until a solution was obtained. The mixture was then removed from the heat source and allowed to cool to below 40° C. with continued mixing. With continuous mixing, Carbopol® 981 was added to the mixture and dispersed. Mixing continued until Carbopol® 981 was fully dispersed and hydrated.

A separate oil phase was made. In a vessel equipped with a mixing implement such as a propeller, diethyl sebacate, halobetasol propionate, and tazarotene were combined. The mixture was agitated until a solution was achieved. With continuous mixing, light mineral oil and sorbitan monooleate were added. Mixing is continued until a solution is obtained.

In a separate vessel, a 1N solution of sodium hydroxide is prepared.

With high speed mixing, the oil phase containing the active ingredients (halobetasol propionate and tazarotene) was added to the aqueous phase. Pemulen™ TR-1 was slowly added into the mixture. Mixing was continued until a homogeneous emulsion was obtained. Mixing speed was decreased and mixing continued for an additional time of 10 minutes to 1 hour. With continuous mixing, an appropriate amount of the sodium hydroxide solution was added incrementally to obtain a pH of 5.5±0.5. Mixing continued further until a homogeneous lotion was obtained, such as for 30 minutes to 3 hours.

Alternatively, Pemulen™ TR-1 may be added into the aqueous phase when it was made.

A clinical study in psoriasis patients was conducted to compare the efficacy of a composition of the present invention containing halobetasol propionate and tazarotene ("IDP-118"); placebo ("Vehicle"); a composition containing only halobetasol propionate ("HP"); and a composition containing only tazarotene ("Taz"). The compositions for the clinical studies are shown in Table 4.

TABLE 4

Compositions for Clinical Studies

| | | Concentration (wt %) | | | |
|---|---|---|---|---|---|
| Ingredient | Function | IDP-118 (Present Invention) | Placebo (Vehicle) | Halobetasol propionate only | Tazarotene only |
| Halobetasol propionate, micronized | Active Ingredient | 0.01 | 0 | 0.01 | 0 |
| Tazarotene | Active Ingredient | 0.045 | 0 | 0 | 0.045 |
| Diethyl sebacate | Emollient & Solvent | 2.97 | 2.97 | 2.97 | 2.97 |
| Light mineral oil | Emollient & Solvent | 8.03 | 8.03 | 8.03 | 8.03 |
| Sorbitan monooleate | Surfactant/ Emulsifying Agent | 0.1 | 0.1 | 0.1 | 0.1 |
| Sorbitol solution, 70% | Humectant | 10.7 | 10.7 | 10.7 | 10.7 |
| Methyl paraben | Antimicrobial Preservative | 0.17 | 0.17 | 0.17 | 0.17 |
| Propyl paraben | Antimicrobial Preservative | 0.03 | 0.03 | 0.03 | 0.03 |
| Edetate disodium dihydrate | Chelating Agent | 0.05 | 0.05 | 0.05 | 0.05 |
| Carbomer copolymer type B (Pemulen™ TR-1) | Emulsifying Agent | 0.4 | 0.4 | 0.4 | 0.4 |
| Carbomer homopolymer type A (Carbomer 981) | Thickener | 0.6 | 0.6 | 0.6 | 0.6 |
| Sodium hydroxide | pH-adjusting agent | q.s. to pH of 5.5 ± 0.5 | q.s. to pH of 5.5 ± 0.5 | q.s. to pH of 5.5 ± 0.5 | q.s. to pH of 5.5 ± 0.5 |
| Purified water | Solvent | q.s. to 100 | q.s. to 100 | q.s. to 100 | q.s. to 100 |

A double blind clinical study was conducted whereby neither the psoriasis patient nor the investigator knew the identity of the test lotion assigned. The blindly labeled lotions were applied to the psoriasis plaques once daily. All test lotions were the same except for the differences is in active ingredients being studied. Approximately 212 subjects were randomized in a 2:2:2:1 ratio to receive IDP-118 (a composition of the present invention, comprising halobetasol propionate 0.01% and tazarotene 0.045%) Lotion, HP (halobetasol propionate 0.01%) Lotion, Taz Lotion (tazarotene 0.045%), and Lotion Vehicle (no active ingredients), as follows:

59 subjects to IDP-118 Lotion ("IDP 118 group")

63 subjects to HP 0.01% Lotion ("HP group")

59 subjects to Taz 0.045% Lotion ("Taz group")

31 subjects to Lotion Vehicle ("Vehicle group").

Eighteen investigative centers participated in the clinical study, each following the same protocol.

The key enrollment criteria were that each subject had at least moderate severity of psoriasis; i.e., a score of 3 or 4, as defined by the Investigator Global Assessment ("IGA") scale shown in Table 5.

TABLE 5

Investigator's Global Assessment

| Score | Grade | Description |
|---|---|---|
| 0 | Clear | No evidence of scaling<br>No evidence of erythema<br>No evidence of plaque elevation above normal skin level |
| 1 | Almost clear | Some plaques with fine scales<br>Faint pink/light red erythema on most plaques<br>Slight or barely perceptible elevation of plaques above normal skin level |
| 2 | Mild | Most to all plaques have some fine scales but are not fully covered, some plaques are completely covered with fine scale<br>Most to all plaques are pink/light red to bright red in color<br>Some plaques have definite elevation above normal skin level, typically with edges that are indistinct and sloped on some of the plaques |

TABLE 5-continued

Investigator's Global Assessment

| Score | Grade | Description |
|---|---|---|
| 3 | Moderate | Some plaques are at least partially covered with a coarse scale, most to all plaques are nearly covered with fine or course scale; Most to all plaques are bright red, some plaque may be dark red in color<br>Definite elevation of most to all plaques; rounded or sloped edges on most of the plaques |
| 4 | Severe | Most to all plaques are covered with coarse, thick scales<br>Most or all plaques are bright, dark or dusky red<br>Almost all plaques are raised and well-demarcated; sharp edges on virtually all plaques |

For each patient the investigator determined and recorded the treatable areas affected by psoriasis at the Baseline visit. Treatable areas were defined as all areas of psoriasis identified at Baseline comprising a body surface area (BSA) of 3% to 12% and designated for treatment with study drug. According to protocol the treatable affected areas did not include the face, scalp, palms, soles, axillae, or intertriginous areas. If palms and soles were affected, study drug could be applied at the discretion of the investigator; however, these areas were not included in the treatable BSA or efficacy assessments. Also a target lesion (psoriasis plaque) was identified and at the Baseline visit to be used solely for assessment of three signs of psoriasis: erythema, plaque elevation, and scaling.

The assigned study drug was applied topically to the affected area (as determined by the investigator at Baseline) once daily for 8 weeks. The initial application was made at the investigational center during the day as per instruction from the study coordinator or designee. The subjects were instructed to avoid exposure to direct sunlight to prevent sunburn. Subjects applied their daily treatments at home as explained by the study coordinator or designee at each investigational center. The subjects were asked to return their used containers of study drug at their clinic visits on Weeks 2, 4, 6, and 8. Subjects were asked to not apply study drug on the day of a clinic visit until after assessments were completed at the clinic. The study coordinator or designee at each investigational center dispensed 2 new containers of study drug to each subject at Baseline and Weeks 2, 4, and 6. Upon completion of the 8-week treatment period all study drug supplies were turned-in to the investigational center, and all subjects were asked to return to the investigational center 4 weeks later for a post-treatment cessation follow-up visit (Week 12). During the study, each subject was only permitted to use approved non-medicated cleansers and moisturizers; no sunscreens or other skin care products were permitted on the treatment areas.

The investigator monitored the efficacy at each study visit by assessing the treatable area and determining the IGA score for psoriasis severity, and grading the target lesion for erythema, plaque elevation, and scaling in each subject.

Information on reported and observed adverse events ("AEs") was obtained at each visit. An abbreviated physical examination was performed at Baseline, Week 8 (end of treatment), and Week 12 (the 4-week post-treatment cessation follow-up visit) for all subjects.

The signs of psoriasis (erythema, plaque elevation, and scaling) were assessed for the selected target lesion using the grading scales displayed in Table 4. Improvements in these signs are a measure of the efficacy of a studied drug. Efficacy assessment was made at 2, 4, 6, and 8 weeks during the treatment phase and at the 12-week visit (the 4-week post treatment follow-up visit).

Tolerability was evaluated through assessments of selected local signs and symptoms (itching, dryness, and burning/stinging). In addition, the treatment areas were examined by the evaluator at each visit for presence or absence of significant known drug-related adverse events: skin atrophy, striae, telangiectasia, and folliculitis.

Efficacy of the four study drugs was assessed based on the IGA scores, that is improvement in the IGA psoriasis severity score over time.

Clinical Efficacy was determined based on the percentage of subjects who were treatment successes.

The IDP-118 group was compared to each of the other treatment groups: (1) HP group, (2) Taz group, and (3) Vehicle group.

To be judged as a treatment success, subjects had to show two-grade improvement in IGA from the baseline, and to have an IGA score of "clear, or almost clear" at the evaluation time. Subjects not achieving treatment success by this standard were considered treatment failures, even though such subjects may have experienced some degree of improvement in their psoriasis.

Results

The efficacy of IDP-118 comprising Halobetasol Propionate 0.01% and Tazarotene 0.045% is shown and discussed.

After completion of the clinical study the blinding codes were broken and the results tabulated. Data for dichotomized IGA with subjects categorized as Treatment Success or Failures are presented in Table 6.

As required by FDA success was defined as at least a two-grade improvement from Baseline in the IGA score and an IGA score equating to 'Clear' or 'Almost Clear'. Also shown in Table 7 is the statistical analysis of IDP-118 compared to each of the other treatment groups based on the percentage of subjects achieving Treatment Success. P-values are from a Cochran-Mantel-Haenszel test using pairwise tests comparing IDP-118 to Vehicle, IDP-118 to HP and IDP-118 to Taz. Week 12 is the follow-up evaluation time, 4 weeks after the end of treatment.

TABLE 6

Treatment Successes and Failures Based on Improvement in IGA Score

| Dichotomized IGA[a] | IDP-118<br>(N = 59) | HP 0.01%<br>(N = 63) | Taz 0.045%<br>(N = 59) | Vehicle<br>(N = 31) |
|---|---|---|---|---|
| Week 2 | | | | |
| No. of Subjects | 59 | 63 | 59 | 31 |
| Success | 7 | 3 | 1 | 0 |
| Failure | 52 | 60 | 58 | 31 |
| p-value[b] | | 0.155 | 0.029 | 0.047 |
| Week 4 | | | | |
| No. of Subjects | 59 | 63 | 59 | 31 |
| Success | 15 | 11 | 1 | 2 |

TABLE 6-continued

Treatment Successes and Failures Based on Improvement in IGA Score

| Dichotomized IGA[a] | IDP-118 (N = 59) | HP 0.01% (N = 63) | Taz 0.045% (N = 59) | Vehicle (N = 31) |
|---|---|---|---|---|
| Failure | 44 | 52 | 58 | 29 |
| p-value[b] |  | 0.285 | <0.001 | 0.030 |
| Week 6 |  |  |  |  |
| No. of Subjects | 59 | 63 | 59 | 31 |
| Success | 19 | 16 | 9 | 1 |
| Failure | 40 | 47 | 50 | 30 |
| p-value[b] |  | 0.408 | 0.031 | 0.002 |
| Week 8 |  |  |  |  |
| No. of Subjects | 59 | 63 | 59 | 31 |
| Success | 31 | 21 | 11 | 3 |
| Failure | 28 | 42 | 48 | 28 |
| p-value[b] |  | 0.033 | <0.001 | <0.001 |
| Week 12 |  |  |  |  |
| No. of Subjects | 55 | 62 | 47 | 29 |
| Success | 21 | 13 | 6 | 2 |
| Failure | 34 | 49 | 41 | 27 |
| p-value[b] |  | 0.042 | 0.004 | 0.002 |

[a]Success was defined as at least a two-grade improvement from Baseline in the IGA score and an IGA score equating to 'Clear' or 'Almost Clear'.
[b]p-value from a Cochran-Mantel-Haenszel test. Pairwise tests were conducted comparing IDP-118 to Vehicle and IDP-118 to HP or Taz.

TABLE 7

Percentage of Subjects Achieving Treatment Success

| Duration | IDP-118 | HP 0.01% | Taz 0.045% | Vehicle |
|---|---|---|---|---|
| Week 2 | 11.9 | 4.8 | 1.7 | 0 |
| Week 4 | 25.4 | 17.5 | 1.7 | 6.5 |
| Week 8 | 52.5 | 33.3 | 18.6 | 9.7 |
| Week 12 | 38.2 | 21.0 | 12.8 | 6.9 |

Actual Clinical Efficacy compared to Predicted Additive Clinical Efficacy (as a percentage of subjects achieving "Treatment Success") is shown in Table 8. The "Treatment Success" percentages for the active treatment groups (IDP-118, HP, and Taz) were corrected for vehicle effect by subtracting the actual Vehicle group results from each to determine the net Treatment Success are shown as a percentage of the number of subjects treated.

TABLE 8

Comparative Treatment Success Rates for IDP-118, HP, and Taz Groups

Control-Adjusted Percentage of Patients Achieving Treatment Success During the Study

| Duration | HP Actual | Taz Actual | HP + Taz Calculated | IDP-118 Actual |
|---|---|---|---|---|
| Week 2 | 4.8 | 1.7 | 6.5 | 11.9 |
| Week 4 | 11 | −4.8 | 6.2 | 18.9 |
| Week 8 | 23.6 | 8.9 | 32.5 | 42.8 |

The synergistic effect of IDP-118 is illustrated by comparing the clinical efficacy from IDP-118 to the predicted efficacy from combining HP and Taz (see Table 9). The control-adjusted percentage of patients who were successfully treated with IDP-118 was greater than the sum of control-adjusted percentages of patients who were successfully treated singly with HP and Taz at all evaluation times: 2 weeks of treatment, 4 weeks of treatment, 8 weeks of treatment, and 4 weeks after the completion of 8 weeks of treatment (Week 12).

TABLE 9

Synergistic Clinical Efficacy of IDP-118 at weeks 2, 4, 8 and 12

| | Percent of Patients Achieving Treatment Success | | Ratio of |
|---|---|---|---|
| Duration | IDP-118 Actual | HP + Taz Calculated | Actual to Expected |
| Week 2 | 11.9 | 6.5 | 1.8 |
| Week 4 | 18.9 | 6.2 | 3.0 |
| Week 8 | 42.8 | 32.5 | 1.3 |
| Week 12 | 31.3 | 20 | 1.6 |

The efficacy of IDP-118 was compared to that of HP (halobetasol propionate 0.01%), Taz (tazarotene 0.045%) and the placebo (vehicle of IDP-118) in terms of success in resolving erythema, plaque elevation, and scaling. The results are shown in Tables 10-12. The success rate for IDP-118 is higher than that of HP, and much higher than those for Taz and placebo. These comparisons were made on assessments of a target lesion that was identified at baseline before treatment was commenced.

The percentage of patients who experienced adverse events, as indicated by itching, burning, and stinging, is much lower for those who were treated with IDP-118 than those treated with HP or Taz. The results are shown in Table 13.

TABLE 10

Severity of Erythema Through Time

| | Baseline | Week 2 | Week 4 | Week 6 | Week 8 | Week 12 |
|---|---|---|---|---|---|---|
| IDP-118 Erythema | | | | | | |
| Number of Subjects | 59 | 59 | 59 | 59 | 59 | 55 |
| 0-None | 0.0% | 0.0% | 10.2% | 6.8% | 11.9% | 16.4% |
| 1-Minimum | 0.0% | 23.7% | 32.2% | 37.3% | 44.1% | 32.7% |
| 2-Mild | 6.8% | 37.3% | 30.5% | 35.6% | 28.8% | 32.7% |
| 3-Moderate | 89.8% | 39.0% | 25.4% | 18.6% | 15.3% | 18.2% |
| 4-Severe | 3.4% | 0.0% | 1.7% | 1.7% | 0.0% | 0.0% |
| HP 0.01% Erythema | | | | | | |
| Number of Subjects | 63 | 63 | 63 | 63 | 63 | 62 |
| 0-None | 0.0% | 3.2% | 7.9% | 12.7% | 14.3% | 11.3% |
| 1-Minimum | 0.0% | 12.7% | 33.3% | 34.9% | 33.3% | 29.0% |
| 2-Mild | 7.9% | 38.1% | 23.8% | 27.0% | 33.3% | 22.6% |
| 3-Moderate | 84.1% | 44.4% | 34.9% | 25.4% | 17.5% | 33.9% |
| 4-Severe | 7.9% | 1.6% | 0.0% | 0.0% | 1.6% | 3.2% |
| Taz 0.045% Erythema | | | | | | |
| Number of Subjects | 59 | 59 | 59 | 59 | 59 | 47 |
| 0-None | 0.0% | 0.0% | 3.4% | 1.7% | 1.7% | 4.3% |
| 1-Minimum | 0.0% | 5.1% | 5.1% | 20.3% | 20.3% | 25.5% |
| 2-Mild | 8.5% | 22.0% | 42.4% | 30.5% | 32.2% | 36.2% |
| 3-Moderate | 81.4% | 57.6% | 37.3% | 39.0% | 37.3% | 34.0% |
| 4-Severe | 10.2% | 15.3% | 11.9% | 8.5% | 8.5% | 0.0% |
| Vehicle (N = 31) Erythema | | | | | | |
| Number of Subjects | 31 | 31 | 31 | 31 | 31 | 29 |

TABLE 10-continued

Severity of Erythema Through Time

|  | Baseline | Week 2 | Week 4 | Week 6 | Week 8 | Week 12 |
|---|---|---|---|---|---|---|
| 0-Clear | 0.0% | 0.0% | 3.2% | 0.0% | 3.2% | 0.0% |
| 1-None | 0.0% | 9.7% | 6.5% | 16.1% | 9.7% | 10.3% |
| 2-Minimum | 6.5% | 25.8% | 19.4% | 12.9% | 25.8% | 34.5% |
| 3-Moderate | 87.1% | 58.1% | 61.3% | 67.7% | 54.8% | 51.7% |
| 4-Severe | 6.5% | 6.5% | 9.7% | 3.2% | 6.5% | 3.4% |

TABLE 11

Degree of Plaque Elevation Through Time

|  | Baseline | Week 2 | Week 4 | Week 6 | Week 8 | Week 12 |
|---|---|---|---|---|---|---|
| IDP-118 Plaque Elevation | | | | | | |
| Number of Subjects | 59 | 59 | 59 | 59 | 59 | 55 |
| 0-None | 0.0% | 10.2% | 28.8% | 33.9% | 40.7% | 32.7% |
| 1-Minimum | 0.0% | 37.3% | 32.2% | 28.8% | 32.2% | 21.8% |
| 2-Mild | 15.3% | 35.6% | 23.7% | 23.7% | 16.9% | 30.9% |
| 3-Moderate | 79.7% | 15.3% | 13.6% | 13.6% | 10.2% | 12.7% |
| 4-Severe | 5.1% | 1.7% | 1.7% | 0.0% | 0.0% | 1.8% |
| HP 0.01% Plaque Elevation | | | | | | |
| Number of Subjects | 63 | 63 | 63 | 63 | 63 | 62 |
| 0-None | 0.0% | 9.5% | 17.5% | 20.6% | 25.4% | 22.6% |
| 1-Minimum | 0.0% | 14.3% | 17.5% | 33.3% | 33.3% | 30.6% |
| 2-Mild | 17.5% | 27.0% | 36.5% | 27.0% | 22.2% | 21.0% |
| 3-Moderate | 73.0% | 44.4% | 27.0% | 17.5% | 17.5% | 22.6% |
| 4-Severe | 9.5% | 4.8% | 1.6% | 1.6% | 1.6% | 3.2% |
| Taz 0.045% Plaque Elevation | | | | | | |
| Number of Subjects | 59 | 59 | 59 | 59 | 59 | 47 |
| 0-None | 0.0% | 3.4% | 3.4% | 5.1% | 5.1% | 10.6% |
| 1-Minimum | 0.0% | 10.2% | 28.8% | 44.1% | 39.0% | 23.4% |
| 2-Mild | 10.2% | 40.7% | 35.6% | 23.7% | 30.5% | 31.9% |
| 3-Moderate | 84.7% | 42.4% | 27.1% | 23.7% | 20.3% | 31.9% |
| 4-Severe | 5.1% | 3.4% | 5.1% | 3.4% | 5.1% | 2.1% |
| Vehicle Plaque Elevation | | | | | | |
| Number of Subjects | 31 | 31 | 31 | 31 | 31 | 29 |
| 0-Clear | 0.0% | 0.0% | 3.2% | 3.2% | 6.5% | 0.0% |
| 1-None | 0.0% | 6.5% | 9.7% | 3.2% | 12.9% | 17.2% |
| 2-Minimum | 12.9% | 29.0% | 22.6% | 29.0% | 19.4% | 37.9% |
| 3-Moderate | 71.0% | 61.3% | 61.3% | 61.3% | 51.6% | 34.5% |
| 4-Severe | 16.1% | 3.2% | 3.2% | 3.2% | 9.7% | 10.3% |

TABLE 12

Degree of Scaling Through Time

|  | Baseline | Week 2 | Week 4 | Week 6 | Week 8 | Week 12 |
|---|---|---|---|---|---|---|
| IDP-118 Scaling | | | | | | |
| Number of Subjects | 59 | 59 | 59 | 59 | 59 | 55 |
| 0-None | 0.0% | 6.8% | 20.3% | 20.3% | 37.3% | 29.1% |
| 1-Minimum | 0.0% | 37.3% | 39.0% | 50.8% | 35.6% | 38.2% |
| 2-Mild | 16.9% | 33.9% | 33.9% | 25.4% | 18.6% | 21.8% |

TABLE 12-continued

Degree of Scaling Through Time

|  | Baseline | Week 2 | Week 4 | Week 6 | Week 8 | Week 12 |
|---|---|---|---|---|---|---|
| 3-Moderate | 76.3% | 20.3% | 6.8% | 3.4% | 8.5% | 10.9% |
| 4-Severe | 6.8% | 1.7% | 0.0% | 0.0% | 0.0% | 0.0% |
| HP 0.01% Scaling | | | | | | |
| Number of Subjects | 63 | 63 | 63 | 63 | 63 | 62 |
| 0-None | 0.0% | 4.8% | 17.5% | 20.6% | 30.2% | 21.0% |
| 1-Minimum | 0.0% | 22.2% | 27.0% | 33.3% | 33.3% | 30.6% |
| 2-Mild | 15.9% | 36.5% | 36.5% | 28.6% | 22.2% | 24.2% |
| 3-Moderate | 73.0% | 33.3% | 17.5% | 15.9% | 12.7% | 21.0% |
| 4-Severe | 11.1% | 3.2% | 1.6%) | 1.6% | 1.6%) | 3.2% |
| Taz 0.045% Scaling | | | | | | |
| Number of Subjects | 59 | 59 | 59 | 59 | 59 | 47 |
| 0-None | 0.0% | 1.7% | 0.0% | 3.4% | 1.7% | 8.5% |
| 1-Minimum | 0.0% | 13.6% | 23.7% | 37.3% | 37.3% | 27.7% |
| 2-Mild | 27.1% | 37.3% | 40.7% | 22.0% | 22.0% | 25.5% |
| 3-Moderate | 62.7% | 39.0% | 30.5% | 33.9% | 35.6% | 36.2% |
| 4-Severe | 10.2%) | 8.5% | 5.1% | 3.4% | 3.4% | 2.1% |
| Vehicle Scaling | | | | | | |
| Number of Subjects | 31 | 31 | 31 | 31 | 31 | 29 |
| 0-Clear | 0.0% | 0.0% | 3.2% | 0.0% | 12.9% | 3.4% |
| 1-None | 0.0% | 6.5% | 19.4% | 19.4% | 16.1% | 17.2% |
| 2-Minimum | 16.1% | 38.7% | 25.8% | 22.6% | 25.8% | 37.9% |
| 3-Moderate | 67.7% | 48.4% | 41.9% | 48.4% | 38.7% | 37.9% |
| 4-Severe | 16.1%) | 6.5% | 9.7% | 9.7% | 6.5% | 3.4% |

TABLE 13

Frequency of Local Skin Reactions Through Time

|  | Baseline | Week 2 | Week 4 | Week 6 | Week 8 | Week 12 |
|---|---|---|---|---|---|---|
| Itching IDP-118 | | | | | | |
| Number of Subjects | 59 | 59 | 57 | 57 | 55 | 55 |
| 0-None | 35.6% | 52.5% | 50.9% | 57.9% | 63.6% | 67.3% |
| 1-Mild | 23.7% | 33.9% | 40.4% | 35.1% | 20.0% | 25.5% |
| 2-Moderate | 39.0% | 11.9%) | 8.8% | 5.3% | 12.7% | 7.3% |
| 3-Severe | 1.7% | 1.7% | 0.0% | 1.8%) | 3.6% | 0.0% |
| HP 0.01% | | | | | | |
| Number of Subjects | 62 | 62 | 62 | 61 | 62 | 62 |
| 0-None | 32.3% | 46.8% | 58.1% | 59.0% | 72.6% | 38.7% |
| 1-Mild | 21.0% | 30.6% | 32.3% | 31.1% | 16.1% | 30.6% |
| 2-Moderate | 32.3% | 19.4% | 9.7% | 9.8% | 11.3% | 21.0% |
| 3-Severe | 14.5% | 3.2% | 0.0% | 0.0% | 0.0% | 9.7% |
| Taz 0.045% | | | | | | |
| Number of Subjects | 58 | 57 | 48 | 49 | 47 | 47 |
| 0-None | 29.3% | 35.1% | 35.4% | 32.7% | 36.2% | 46.8% |
| 1-Mild | 22.4% | 26.3% | 31.3% | 36.7% | 34.0% | 38.3% |
| 2-Moderate | 41.4% | 26.3% | 27.1% | 24.5% | 23.4% | 12.8% |
| 3-Severe | 6.9% | 12.3% | 6.3% | 6.1% | 6.4% | 2.1% |
| Vehicle | | | | | | |
| Number of Subjects | 31 | 31 | 31 | 31 | 30 | 29 |
| 0-None | 22.6% | 35.5% | 45.2% | 38.7% | 33.3% | 48.3% |
| 1-Mild | 29.0% | 35.5% | 25.8% | 25.8% | 33.3% | 27.6% |

TABLE 13-continued

Frequency of Local Skin Reactions Through Time

|  | Baseline | Week 2 | Week 4 | Week 6 | Week 8 | Week 12 |
|---|---|---|---|---|---|---|
| 2-Moderate | 38.7% | 19.4% | 16.1% | 25.8% | 23.3% | 20.7% |
| 3-Severe | 9.7% | 9.7% | 12.9% | 9.7% | 10.0% | 3.4% |
| Burning/ Stinging IDP-118 | | | | | | |
| Number of Subjects | 59 | 59 | 57 | 57 | 55 | 55 |
| 0-None | 71.2% | 79.7% | 73.7% | 77.2% | 70.9% | 89.1% |
| 1-Mild | 10.2% | 13.6% | 15.8% | 12.3% | 21.8% | 10.9% |
| 2-Moderate | 18.6% | 6.8% | 10.5% | 8.8% | 7.3% | 0.0% |
| 3-Severe | 0.0% | 0.0% | 0.0% | 1.8% | 0.0% | 0.0% |
| HP 0.01% | | | | | | |
| Number of Subjects | 62 | 62 | 62 | 61 | 62 | 62 |
| 0-None | 62.9% | 77.4% | 79.0% | 88.5% | 91.9% | 83.9% |
| 1-Mild | 11.3% | 14.5% | 16.1% | 9.8% | 6.5% | 9.7% |
| 2-Moderate | 19.4% | 6.5% | 4.8% | 1.6% | 1.6% | 4.8% |
| 3-Severe | 6.5% | 1.6% | 0.0% | 0.0% | 0.0% | 1.6% |
| Taz 0.045% | | | | | | |
| Number of Subjects | 58 | 57 | 48 | 49 | 47 | 47 |
| 0-None | 72.4% | 63.2% | 64.6% | 57.1% | 68.1% | 85.1% |
| 1-Mild | 10.3% | 17.5% | 18.8% | 30.6% | 19.1% | 10.6% |
| 2-Moderate | 17.2% | 12.3% | 14.6% | 8.2% | 12.8% | 4.3% |
| 3-Severe | 0.0% | 7.0% | 2.1% | 4.1% | 0.0% | 0.0% |
| Vehicle | | | | | | |
| Number of Subjects | 31 | 31 | 31 | 31 | 30 | 29 |
| 0-None | 54.8% | 71.0% | 74.2% | 71.0% | 76.7% | 72.4% |
| 1-Mild | 19.4% | 19.4% | 16.1% | 22.6% | 3.3% | 6.9% |
| 2-Moderate | 22.6% | 6.5% | 3.2% | 3.2% | 13.3% | 17.2% |
| 3-Severe | 3.2% | 3.2% | 6.5% | 3.2% | 6.7% | 3.4% |

IDP-118 was consistently more effective than HP 0.01%, Taz 0.045%, or vehicle in achieving treatment success, defined as at least a two-grade improvement from Baseline in the IGA score at baseline and a score of Clear or Almost Clear at the evaluation time. IDP-118 demonstrated statistically significant superiority over vehicle as early as two weeks after starting treatment. At Week 8 end of treatment, 52.5% of subjects in the IDP-118 group had treatment success compared with 33.3% in the HP group, 18.6% in the Taz group, and 9.7% in the Vehicle group (see Table 5). Pairwise tests comparing IDP-118 with vehicle and HP 0.01% or Taz 0.045% showed statistically significant treatment group differences at both Week 8 (end of treatment) and Week 12 (4-week post-treatment follow-up). Of the subjects in the IDP-118 group who achieved treatment success at Week 8, more than half maintained status (treatment success) at Week 12 some four weeks after the completion of daily application of the test material, demonstrating the absence of a corticosteroid rebound effect.

Mean absolute and percent changes in the IGA score from Baseline at each visit were consistent with the results of the dichotomized IGA. At Week 8, the mean change from Baseline IGA score was −1.42 in the IDP-118 group compared with −1.24 in the HP group, −0.64 in the Taz group, and −0.42 in the Vehicle group.

There were no serious adverse reactions reported in any of the patients treated with IDP-118 during the eight-week period of daily application of the composition or the four-week medication-free follow-up period.

In another aspect, the present invention provides a method for treating psoriasis. The method comprises topically applying to an affected area of the body of a subject suffering from psoriasis any one of the compositions of the present invention, as disclosed herein, one or more times per day for a period of time sufficient to treat such psoriasis. For example, such a period of time may be 1 to 30 days or longer as needed For example, such a period of time may be one week, two weeks, four weeks, eight weeks, twelve weeks, or longer as needed. For example, a composition of the present invention is applied topically to affected areas of the body once per day for 7-14 days. Alternatively, it may be applied two or three times per day for 7-14 days. Alternatively, it may be applied once per day for one week to six months. For example, it may be applied once per day for two weeks, four weeks, eight weeks, or twelve weeks. In one embodiment, the treatment may be stopped for 1-7 days (e.g., 2, 3, 4, 5, 6, or 7 days) after an extended treatment period before it is resumed for another extended treatment period. Such an extended period may be 7 days, 7-14 days, 7-21 days, 7-30 days, or longer before more treatment is needed or desired.

In yet another aspect, the present invention provides a method of treating psoriasis topically with pharmaceutical composition comprising a combination of: (a) halobetasol or a pharmaceutically acceptable salt or ester thereof; and (b) a tazarotene or a pharmaceutically acceptable tazarotenic acid salt, or ester; wherein each of: (a) halobetasol or a pharmaceutically acceptable salt, or ester thereof; and (b) tazarotene or a pharmaceutically acceptable tazarotenic acid salt, or ester is present in the composition at a positive concentration of less than 0.05% based on the weight of the composition; wherein the clinical efficacy of the combination is greater than that of either the halobetasol component or the tazarotene component at the same concentration when used alone.

In yet another aspect, the present invention provides a method of treating psoriasis topically with pharmaceutical composition comprising a combination of: (a) halobetasol or a pharmaceutically acceptable salt, or ester thereof; and (b) a tazarotene or a pharmaceutically acceptable tazarotenic acid salt, or ester; wherein each of: (a) halobetasol or a pharmaceutically acceptable salt, or ester thereof; and (b) tazarotene or a pharmaceutically acceptable tazarotenic acid salt, or ester is present in the composition at a positive concentration of less than 0.05% based on the weight of the composition; wherein the clinical success rate of the combination is synergistic compared to the clinical success rate of the halobetasol component at the same concentration used alone plus the clinical success rate of the tazarotene component used alone at the same concentration.

In yet another aspect, the present invention provides topical pharmaceutical compositions comprising a combination of: (a) halobetasol or a pharmaceutically acceptable salt, or ester thereof; and (b) a tazarotene or a pharmaceutically acceptable tazarotenic acid salt, or ester thereof, and methods using the same, for treating psoriasis; wherein the pharmaceutical composition is a cream, lotion, ointment, gel, shampoo, suspension, paste, plaster, foam, spray or solution. Prophetic examples of formulations of some of these types are illustrated in Table 14.

In yet another aspect, the present invention provides a method of treating psoriasis topically with pharmaceutical composition comprising a combination of: (a) halobetasol or a pharmaceutically acceptable salt, or ester thereof; and (b) a tazarotene or a pharmaceutically acceptable tazarotenic acid salt, or ester; wherein the composition is applied at least once daily for 4 weeks, such as for 6 weeks or 8 weeks.

In yet another aspect, the present invention provides a method of treating psoriasis topically with pharmaceutical composition comprising a combination of: (a) halobetasol or a pharmaceutically acceptable salt, or ester thereof; and (b) a tazarotene or a pharmaceutically acceptable tazarotenic acid salt, or ester; wherein the composition is applied once daily for more than 2 weeks, such as 4 weeks, for 6 weeks or for 8 weeks without any serious adverse events (side effects).

In yet another aspect, a composition of the present invention that can be used in any of the methods disclosed herein can be in the form of a solution, a spray, a milk, a foam, or an ointment. Non-limiting examples of these compositions are shown in Table 14.

TABLE 14

Examples of Various Dosage Forms of Compositions of the Present Invention

| Ingredient | Solution | Spray | Milk | Foam | Ointment |
| --- | --- | --- | --- | --- | --- |
| | | | Concentration (% wt) | | |
| Corticosteroid | 0.001-0.049 | 0.001-0.049 | 0.001-0.049 | 0.001-0.049 | 0.001-0.049 |
| Tazarotene or tazarotenic acid | 0.01-0.049 | 0.01-0.049 | 0.01-0.049 | 0.01-0.049 | 0.01-0.049 |
| Humectant | 0-15.0 | 0-15.0 | 0-15.0 | 0-15.0 | — |
| Antimicrobial preservative | 0.01-0.4 | 0.01-0.4 | 0.01-0.4 | 0.01-0.4 | — |
| Chelating agent | 0.02-0.1 | 0.02-0.1 | 0.02-0.1 | 0.02-0.1 | — |
| Emollients/Lipophilic Solvents | qsad 100 | 0.5-50.0 | 0.5-50.0 | 0.5-50.0 | 0.5-50.0 |
| Volatile solvent | — | qsad 100 | — | — | — |
| Non-ionic polyethoxylated compounds | — | — | — | — | — |
| Non-ionic sorbitan compounds | — | — | 0.5-5.0 | — | 0.5-5.0 |
| Polyoxyethylene fatty ethers | — | — | — | 0.5-10.0 | — |
| Fatty alcohols | — | — | — | 1-8.0 | 1.0-10.0 |
| Petrolatum | — | — | — | — | qsad 100 |
| Pharmaceutical aids (pH adjustment) | — | — | 0.1-5.0 | 0.1-5.0 | — |
| Purified water | — | — | qsad 100 | qsad 100 | — |

In still another aspect, a composition of the present invention may be used in conjunction with another method of treatment of psoriasis, such as phototherapy (e.g., with ultraviolet light).

In yet another aspect, a composition of the present invention may be used in conjunction with another medicament for treating psoriasis. Such other medicament may be an anti-TNF-α agent (e.g., infliximab, etanercept, adalimumab, or golimumab), an agent targeting the Th17/IL-23 axis (e.g., ustekinumab or briakinumab), a protein kinase C inhibitor (e.g., AEB071), a mitogen-activated protein kinase inhibitor (e.g., BMS-582949), a FMS-like tyrosine kinase inhibitor (e.g., lestaurtinib), a Janus kinase inhibitor tofacitinib, ASP-015K, or INCB018424), a phosphodiesterase 4 inhibitor (e.g., apremilast, AN2728, or MK0873), a nerve growth factor inhibitor (e.g., CF101), an anti-folate agent (e.g., methotrexate, aminopterin, or BCX-4208), a calcineurin inhibitor (e.g., cyclosporine), an anti-angiogenic agent (e.g., anti-VEGF antibody or soluble VEGFR), or a vitamin D analog or derivative. Such other medicament may be administered to a patient at substantially the same time or at a different time. Such other medication may be administered topically, orally, or by injection or infusion.

While the present disclosure shows and describes a number of exemplary embodiments, it will be manifest to those skilled in the art that various further modifications may be made without departing from the spirit and scope of the underlying inventive concept and that the same is not limited to particular compositions, processes, methods, or structures herein shown and described.

What is claimed is:

1. A topical pharmaceutical composition for treating psoriasis, the composition comprising:
   halobetasol propionate at a concentration of 0.01 percent by weight of the composition;
   tazarotene at a concentration of 0.045 percent by weight of the composition;
   a liquid oil component, wherein the liquid oil component comprises one or more materials that are practically insoluble or insoluble in water and which are liquid at room temperature of 22° C.; and
   an aqueous component;
   wherein the pharmaceutical composition is formulated as a lotion.

2. The pharmaceutical composition of claim 1, wherein the halobetasol propionate is dissolved in the liquid oil component at room temperature.

3. The pharmaceutical composition of claim 1, wherein the tazarotene is dissolved in the liquid oil component at room temperature.

4. The pharmaceutical composition of claim 1, wherein the liquid oil component comprises a dicarboxylic acid ester, a monocarboxylic ester, or a combination thereof.

5. The pharmaceutical composition of claim 4, wherein the liquid oil component comprises a dicarboxylic acid ester.

6. The pharmaceutical composition of claim 4, wherein the liquid oil component comprises a monocarboxylic acid ester.

7. The pharmaceutical composition of claim 4, wherein the liquid oil component further comprises mineral oil or light mineral oil.

8. The pharmaceutical composition of claim 7, wherein the liquid oil component further comprises light mineral oil.

9. The pharmaceutical composition of claim 1, wherein the composition further comprises one or more humectants, preservatives, chelating agents, emulsifying agents, and/or thickening agents.

10. The pharmaceutical composition of claim 9, wherein the composition further comprises an emulsifying agent.

11. The pharmaceutical composition of claim 1, wherein the composition further comprises a pH adjusting agent.

12. The pharmaceutical composition of claim 1, wherein the composition is capable of providing a synergistic efficacy when the composition is used to treat psoriasis.

13. The pharmaceutical composition of claim 1, wherein the composition is capable of providing a synergistic reduction is at least one adverse event when the composition is used to treat psoriasis, wherein the adverse event is selected from the group consisting of itching, burning, stinging, and combinations thereof.

14. A pharmaceutical composition for topical application to the skin of an individual, the composition comprising:

halobetasol propionate at a concentration of 0.01 percent by weight of the composition;

tazarotene at a concentration of 0.045 percent by weight of the composition;

a liquid oil component, wherein the liquid oil component comprises a dicarboxylic acid ester, a monocarboxylic acid ester, or a combination thereof; and an aqueous component;

wherein the pharmaceutical composition is formulated as a lotion.

15. The topical pharmaceutical composition of claim 14, wherein the composition further comprises a surfactant, an emulsifying agent, a thickening agent, a humectant, one or more antimicrobial preservatives, a chelating agent, and a pH-adjusting agent.

16. A topical pharmaceutical composition for treating psoriasis, the composition comprising:

halobetasol propionate at a concentration of 0.01 percent by weight of the composition;

tazarotene at a concentration of 0.045 percent by weight of the composition;

a liquid oil component, wherein the liquid oil component comprises a dicarboxylic acid ester, a monocarboxylic acid ester, or a combination thereof, and light mineral oil; and an aqueous component, wherein the aqueous component comprises purified water;

a carbomer copolymer type B; and a carbomer homopolymer type A;

wherein the pharmaceutical composition is formulated as a lotion.

17. The topical pharmaceutical composition of claim 16, wherein the composition further comprises a humectant, one or more antimicrobial preservatives, a chelating agent, and a pH-adjusting agent.

18. A method for treating psoriasis, the method comprising topically applying a pharmaceutical composition to an affected area on a body of a subject suffering from psoriasis, wherein the composition comprises:

halobetasol propionate at a concentration of 0.01 percent by weight of the composition;

tazarotene at a concentration of 0.045 percent by weight of the composition;

a liquid oil component, wherein the liquid oil component comprises one or more materials that are practically insoluble or insoluble in water and which are liquid at room temperature of 22° C.; and an aqueous component;

wherein the pharmaceutical composition is formulated as a lotion; and wherein the composition is capable of providing synergistic efficacy.

19. The method of claim 18, wherein said applying is carried out once daily for longer than two weeks.

20. The method of claim 19, wherein the method continues to provide relief for a period of four weeks after eight weeks of applying the composition to the affected area on the body of the subject.

21. The method of claim 18, wherein said applying is carried out once daily for twelve weeks.

22. The method of claim 18, wherein the halobetasol propionate is dissolved in the liquid oil component at room temperature, wherein the tazarotene is dissolved in the liquid oil component at room temperature, or wherein both the halobetasol propionate and the tazarotene are dissolved in the liquid oil component at room temperature.

23. The method of claim 18, wherein the liquid oil component comprises a dicarboxylic acid ester, a monocarboxylic ester, or a combination thereof.

24. The method of claim 23, wherein the liquid oil component comprises a dicarboxylic acid ester.

25. The method of claim 23, wherein the liquid oil component comprises a monocarboxylic acid ester.

26. The method of claim 23, wherein the liquid oil component further comprises mineral oil or light mineral oil.

27. The method of claim 23, wherein the liquid oil component further comprises light mineral oil.

28. The method of claim 18, wherein the composition further comprises one or more humectants, preservatives, chelating agents, emulsifying agents, thickening agents, and/or a pH adjusting agent.

29. The method of claim 28, wherein the composition further comprises an emulsifying agent.

30. The method of claim 18, wherein the composition is capable of providing a synergistic reduction is at least one adverse event, wherein the adverse event is selected from the group consisting of itching, burning, stinging, and combinations thereof.

* * * * *